United States Patent
Yong

(10) Patent No.: US 10,675,259 B2
(45) Date of Patent: Jun. 9, 2020

(54) DRUG COMBINATION WITH ANTITUMOR EFFECTS

(71) Applicant: DONGGUAN ANHAO PHARMACEUTICAL CO., LTD., Dongguan, Guangdong (CN)

(72) Inventor: Zhiquan Yong, Guangdong (CN)

(73) Assignee: DONGGUAN ANHAO PHARMACEUTICAL CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/781,987

(22) PCT Filed: Sep. 1, 2016

(86) PCT No.: PCT/CN2016/097789
§ 371 (c)(1),
(2) Date: Jun. 6, 2018

(87) PCT Pub. No.: WO2018/035884
PCT Pub. Date: Mar. 1, 2018

(65) Prior Publication Data
US 2018/0353449 A1 Dec. 13, 2018

(30) Foreign Application Priority Data

Aug. 26, 2016 (CN) .......................... 2016 1 0739597

(51) Int. Cl.
| | | |
|---|---|---|
| *A61K 31/192* | (2006.01) |
| *A61K 38/14* | (2006.01) |
| *A61K 45/06* | (2006.01) |
| *A61K 31/282* | (2006.01) |
| *A61K 31/337* | (2006.01) |
| *A61K 31/44* | (2006.01) |
| *A61K 31/675* | (2006.01) |
| *A61P 35/00* | (2006.01) |
| *A61P 35/04* | (2006.01) |
| *A61K 31/704* | (2006.01) |
| *A61K 31/351* | (2006.01) |

(52) U.S. Cl.
CPC .......... *A61K 31/192* (2013.01); *A61K 31/282* (2013.01); *A61K 31/337* (2013.01); *A61K 31/44* (2013.01); *A61K 31/675* (2013.01); *A61K 31/704* (2013.01); *A61K 38/14* (2013.01); *A61K 45/06* (2013.01); *A61P 35/00* (2018.01); *A61P 35/04* (2018.01); *A61K 31/351* (2013.01); *A61K 2300/00* (2013.01)

(58) Field of Classification Search
CPC ......... A61K 31/192; A61P 35/04; A61P 35/00
USPC ........................................................ 514/557
See application file for complete search history.

(56) References Cited

U.S. PATENT DOCUMENTS

| | | | | |
|---|---|---|---|---|
| 3,590,028 A | * | 6/1971 | Arcamone et al. | C07H 15/252 435/78 |
| 4,140,707 A | * | 2/1979 | Cleare | C07F 15/0093 546/2 |

FOREIGN PATENT DOCUMENTS

CN 101074189 A * 11/2007

OTHER PUBLICATIONS

English Translation of CN 101074189 A (2007).*
Sanghee Kim et al., "Comparative Molecular Field Analysis Study of Stilbene Derivatives Active against A549 Lung Carcinoma", Chem, Pharm. Bull. 51(5) 516-521 (2003), vol. 51, No. 5, pp. 516-520.
Christine Borrel et al., "New antitubulin derivatives in the combretastatin A4 series: synthesis and biological evaluation", Bioorganic & Medicinal Chemistry 13 (2005), pp. 3853-3864.

* cited by examiner

*Primary Examiner* — Kevin E Weddington
(74) *Attorney, Agent, or Firm* — Novick, Kim & Lee, PPLC; Allen Xue

(57) ABSTRACT

A drug combination with antitumor effects, contains styrene acid derivatives and antitumor medicaments with same or different specifications of unit preparations that can be simultaneously or separately administrated, as well as pharmaceutically acceptable carriers. The joint use of trans-styrene acid derivatives and antitumor drugs provides synergistic action, and the use of trans-styrene acid derivatives combined with a part of antitumor drugs can further exert the toxicity attenuation effects, showing a good clinical application prospect.

6 Claims, No Drawings

DRUG COMBINATION WITH ANTITUMOR EFFECTS

TECHNICAL FIELD

The present invention relates to a drug combination with antitumor effects.

BACKGROUND ART

Malignant tumor is the major killer for current human health, and one of the most serious diseases presenting the grave threat to human lives. Combined therapy of tumor is mainly surgical procedures, radiation therapy, and tumor chemotherapy. Drugs play a key role in the chemotherapy of cancer. During the past few years, the research and development of antitumor drugs have made a great progress, and in the last century, the use of carboplatin, paclitaxel and so on made certain specific tumors have very high recovery rate. But, since antitumor drugs have poor selectivity, high toxic and side effects, drug resistance, and same defects, at present, above half of tumor patients do not response to the treatment or are resistant to drugs, finally leading to the treatment failure, especially for the treatment of solid tumors.

Trans-styrene acid derivatives have antitumor action, but the effect of single use is not satisfactory.

CONTENT OF THE INVENTION

The object of the present invention is to provide a drug combination with antitumor effects, and to overcome the problem that the antitumor effect is not good when trans-styrene acid derivatives are separately used and other available antitumor drugs are singly used respectively.

For the drug combination with antitumor effects according to the present invention, it contains styrene acid derivatives and antitumor medicaments with same or different specifications of unit preparations that can be simultaneously or separately administrated, as well as pharmaceutically acceptable carriers;

The structures of said styrene acid derivatives are shown in formula (I):

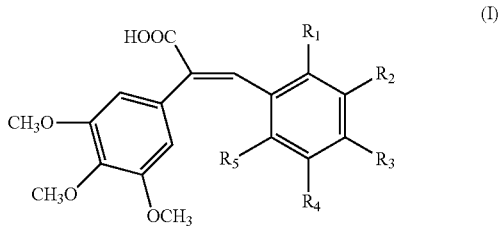

Wherein, $R_1$, $R_2$, $R_3$, $R_4$, and $R_5$ are preferably hydrogen, hydroxyl group, and methoxyl group, in which $R_1$ is more preferably hydrogen, $R_2$ is hydroxyl group, $R_3$ is methoxyl group, $R_4$ is hydrogen, and $R_5$ is hydrogen. Said styrene acid derivatives have a cis- or trans-structure, in which trans-structure is preferable.

Preferably, said trans-styrene acid derivative is (E)-3-(2',3'-dihydroxyl-4'-methoxylphenyl)-2-(3'',4'',5''-trimethoxyl-phenyl)-2-acrylic acid.

Trans-styrene acid derivative is (E)-3-(2',3'-dihydroxyl-4'-methoxylphenyl)-2-(3'',4'',5''-trimethoxylphenyl)-2-acrylic acid, recorded in the patent document with a publication number 101074189B, and it can be prepared as the method disclosed in the patent.

Preferably, said antitumor drugs are selected from the group of alkylating agents, platinum complexes, antineoplastic antibiotics, paclitaxel and its derivatives, and sorafenib.

Preferably, said alkylating agent is cyclophosphamide; said platinum complex is carboplatin; said antineoplastic antibiotic is adriamycin or bleomycin hydrochloride; said paclitaxel derivative is docetaxel.

Preferably, the weight ratio of styrene acid derivatives and antitumor medicaments is in the range of 1:1 to 640:1.

Preferably, when the antitumor drug is carboplatin, the weight ratio of styrene acid derivative and antitumor drug is 112:1;

When the antitumor drug is paclitaxel, the weight ratio of styrene acid derivative and antitumor drug is in the range of 1:1-840:11;

When the antitumor drug is sorafenib, the weight ratio of styrene acid derivative and antitumor drug is 5:1;

When the antitumor drug is cyclophosphamide, the weight ratio of styrene acid derivative and antitumor drug is 65:60;

When the antitumor drug is adriamycin, the weight ratio of styrene acid derivative and antitumor drug is 4400:9;

When the antitumor drug is docetaxel, the weight ratio of styrene acid derivative and antitumor drug is 640:1;

When the antitumor drug is bleomycin hydrochloride, the weight ratio of styrene acid derivative and antitumor drug is 400:1.

The present invention further provides the use of said drug combination in the preparation of medicaments for the treatment of lung cancer, liver cancer, ovarial caner, melanoma, colon cancer, kidney cancer, and bladder cancer. Wherein, said drug for the treatment of lung cancer is that treating small cell lung cancer.

The present invention provides the use of trans-styrene acid derivatives and antitumor medicaments in the preparation of antitumor medicaments;

The structures of said styrene acid derivatives are shown in formula (I):

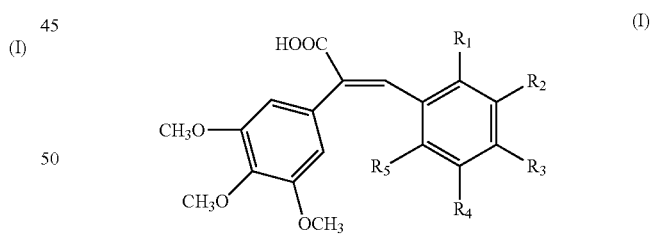

Wherein, $R_1$, $R_2$, $R_3$, $R_4$, and $R_5$ are preferably hydrogen, hydroxyl group, and methoxyl group, in which $R_1$ is more preferably hydrogen, $R_2$ is hydroxyl group, $R_3$ is methoxyl group, $R_4$ is hydrogen, and $R_5$ is hydrogen. Said styrene acid derivatives have a cis- or trans-structure, in which trans-structure is preferable.

Preferably, said trans-styrene acid derivative is (E)-3-(2',3'-dihydroxyl-4'-methoxylphenyl)-2-(3'',4'',5''-trimethoxyl-phenyl)-2-acrylic acid.

Preferably, said antitumor drugs are selected from the group of alkylating agents, platinum complexes, antineoplastic antibiotics, paclitaxel and its derivatives, and sorafenib.

Preferably, said alkylating agent is cyclophosphamide; said platinum complex is carboplatin; said antineoplastic antibiotic is adriamycin or bleomycin hydrochloride; said paclitaxel derivative is docetaxel.

Preferably, the weight ratio of styrene acid derivatives and antitumor medicaments is in the range of 1:1 to 640:1.

Further preferably, when the antitumor drug is carboplatin, the weight ratio of styrene acid derivative and antitumor drug is 112:1;

When the antitumor drug is paclitaxel, the weight ratio of styrene acid derivative and antitumor drug is in the range of 1:1-840:11;

When the antitumor drug is sorafenib, the weight ratio of styrene acid derivative and antitumor drug is 5:1;

When the antitumor drug is cyclophosphamide, the weight ratio of styrene acid derivative and antitumor drug is 65:60;

When the antitumor drug is adriamycin, the weight ratio of styrene acid derivative and antitumor drug is 4400:9;

When the antitumor drug is docetaxel, the weight ratio of styrene acid derivative and antitumor drug is 640:1;

When the antitumor drug is bleomycin hydrochloride, the weight ratio of styrene acid derivative and antitumor drug is 400:1.

Wherein, said drug combination is that used for the treatment of lung cancer, liver cancer, ovarial caner, melanoma, colon cancer, kidney cancer, and bladder cancer.

Wherein, said drugs for the treatment of lung cancer are those treating small cell lung cancer.

One method for the treatment of tumor, containing the following steps: styrene acid derivatives and antitumor medicaments with same or different specifications of unit preparations are simultaneously or separately administrated;

The structures of said styrene acid derivatives are shown in formula (I):

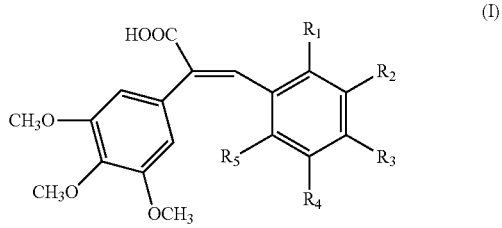

Wherein, $R_1$, $R_2$, $R_3$, $R_4$, and $R_5$ are preferably hydrogen, hydroxyl group, and methoxyl group, in which $R_1$ is more preferably hydrogen, $R_2$ is hydroxyl group, $R_3$ is methoxyl group, $R_4$ is hydrogen, and $R_5$ is hydrogen. Said styrene acid derivatives have a cis- or trans-structure, in which trans-structure is preferable.

Preferably, said trans-styrene acid derivative is (E)-3-(2', 3'-dihydroxyl-4'-methoxyphenyl)-2-(3",4",5"-trimethoxyl-phenyl)-2-acrylic acid.

Preferably, said antitumor drugs are selected from the group of alkylating agents, platinum complexes, antineoplastic antibiotics, paclitaxel and its derivatives, and sorafenib.

Preferably, said alkylating agent is cyclophosphamide; said platinum complex is carboplatin; said antineoplastic antibiotic is adriamycin or bleomycin hydrochloride; said paclitaxel derivative is docetaxel.

Preferably, the weight ratio of styrene acid derivatives and antitumor medicaments is in the range of 1:1 to 640:1.

Further preferably, when the antitumor drug is carboplatin, the weight ratio of styrene acid derivative and antitumor drug is 112:1;

When the antitumor drug is paclitaxel, the weight ratio of styrene acid derivative and antitumor drug is in the range of 1:1-840:11;

When the antitumor drug is sorafenib, the weight ratio of styrene acid derivative and antitumor drug is 5:1;

When the antitumor drug is cyclophosphamide, the weight ratio of styrene acid derivative and antitumor drug is 65:60;

When the antitumor drug is adriamycin, the weight ratio of styrene acid derivative and antitumor drug is 4400:9;

When the antitumor drug is docetaxel, the weight ratio of styrene acid derivative and antitumor drug is 640:1;

When the antitumor drug is bleomycin hydrochloride, the weight ratio of styrene acid derivative and antitumor drug is 400:1.

The drug combination can be used by gastrointestinal administration such as intravenous, subcutaneous, and intramuscular routes, and in order to improve efficiency, the administration by intravenous and subcutaneous routes is preferable.

The present invention further provides the use of the method mentioned above in the treatment of lung cancer, liver cancer, ovarial caner, melanoma, colon cancer, kidney cancer, and bladder cancer. Wherein, said drugs for the treatment of lung cancer are those treating small cell lung cancer.

The joint use of trans-styrene acid derivatives and antitumor drugs according to the present invention can provide synergistic action, and the use of trans-styrene acid derivatives combined with a part of antitumor drugs can further exert the toxicity attenuation effects. The therapeutic effect of drug combination prepared with trans-styrene acid derivatives and antitumor drugs is good, and the toxicity is low, with a good clinical application prospect.

In the following, the present invention is further illustrated by referring to the specific examples, but the present invention is not limited. Without departing from above basic technical spirit of the present invention, various modifications, alternations or changes, made according to the common technical knowledge and conventional means in the art, can also be realized.

EXAMPLES

Calculation formula:

Tumor long diameter a (mm), as well as its vertical short diameter b (mm), is measured twice a week, and the calculation formula of tumor volume is $TV = ab^2/2$, while the calculation formula of relative tumor volume is $RTV = V_t/V_o$, in which $V_o$ is the tumor volume measured when caged (i.e. d1), and $V_t$ is the tumor volume measured every time.

Results are determined based on the following formula:

$$\text{tumor control rate \%} = \frac{\text{The mean } RTV \text{ of control group} - \text{The mean } RTV \text{ of test group}}{\text{The mean } RTV \text{ of control group}} \times 100$$

Evaluation criteria (calculating Q value by Jin's formula):

$$Q = \frac{E_{a+b}}{E_a + E_b - E_a \times E_b}$$

Ea+b is the tumor inhibitory rate caused by the drug combination, while Ea and Eb are the tumor inhibitory rates caused by drug A and drug B, respectively. If Q value is in the range of 0.85~1.15, the result is additive (+); if Q value>1.15, the result is enhanced (++).

Example 1

The Therapeutic Effect of DX1002 Combined with CBP Against Human Lung Cancer 95D Transplanted in Nude Mice 1. Experimental Materials Reagent: Carboplatin injection (Bobei, CBP, batch number WB1J1411012, specification 10 ml:50 mg), produced by QiLu Pharmaceutical Co. Ltd, diluted to the required concentration with sterile normal saline before use.

DX1002: (E)-3-(2',3'-dihydroxyl-4'-methoxylphenyl)-2-(3",4",5"-trimethoxylphenyl)-2-acrylic acid. Preparative method: 3,4,5-trimethoxylphenylacetic acid (140 g, 610 mmol), 2,3-dihydroxyl-4-methoxylbenzaldehyde (724 mmol), acetic anhydride (200 ml), and $NEt_3$ (100 ml, 717 mmol) were added into a round bottom flask (1000 ml), stirred and refluxed for 2.5 h at the temperature of 150° C. The solvent was evaporated under reduced pressure, to obtain the oil, to which 1 N hydrochloric acid (about 300 ml) was added. The mixture was stirred overnight at room temperature, to obtain the yellow solid, and after recrystallization in ethanol (400 ml), yellowy solids were provided (DX1002, purity>98%).

Animals: BALB/C nude mice (SPF grade, body weight: 19-21 g, male).

Animal number: 8 mice/group.

Tumor cell lines: human lung cancer 95D cell lines provided by West China Medical Center of Sichuan University.

2. Experimental Method

Well-grown lung cancer 95D tumor block was taken out, and cut into 3 mm equal blocks under sterile conditions. Each mouse was subcutaneously inoculated a block under right axilla with trocar. Four groups were included, and each test group has 8 mice, while the control group has more than 8 mice:

Group 1: DX1002 400 mg/kg/day (ig×14 days)
Group 2: CBP 10 mg/kg/day (ip×10 days, injected every other day)
Group 3: DX1002+CBP
Group 4: Control 13 days after inoculation, the mean volume of tumor block was found to be about 100 $mm^3$, and animals were regrouped based on the tumor size. Animals with too large or too small tumors were eliminated, and the mean tumor volume in each group was almost identical. Drugs were administrated as above schedule, and given by gavage for successive 14 days, with a volume of 0.5 ml/20 g body weight. CBP was intraperitoneally (ip) administered, and injected every other day for total 10 days. From day 14 after inoculation, tumor long diameter a (mm), as well as its vertical short diameter b (mm), is measured twice a week using electronic digital caliper rule, and the calculation formula of tumor volume is $TV=ab^2/2$, while the calculation formula of relative tumor volume is $RTV=V_t/V_o$, in which $V_o$ is the tumor volume measured when caged (i.e. d1), and $V_t$ is the tumor volume measured every time. 29 days after inoculation (d17), all animals were sacrificed and weighed.

3. Experimental Results

Experimental results are shown in Table 1:

TABLE 1

The tumor inhibitory effect of DX1002 combined with CBP against human lung cancer 95D transplanted in nude mice ($\bar{x} \pm SD$)

| Groups | Dose (mg/kg) | Dosage regimen | Animal numbers beginning/end | Body weight of animals (g) | RTV (d 17) | Tumor inhibitory rate (%) | Q |
|---|---|---|---|---|---|---|---|
| Control | — | — | 14/14 | 26.69 ± 1.40 | 6.69 ± 1.40 | — | |
| CBP | 10 × 5 | ip × 5 | 8/8 | 22.89 ± 0.68** | 3.89 ± 0.68** | 41.85 | |
| DX1002 | 400 × 14 | ig × 14 | 8/8 | 23.67 ± 0.44** | 2.90 ± 0.44** | 56.65 | |
| DX1002 + CBP | 400/10 | ig × 14/ip × 5 | 8/8 | 22.53 ± 0.33** | 0.88 ± 0.33** | 86.85 | 1.16 |

Compared with the control group:
*P < 0.05,
**P < 0.01.

From Table 1, it can be seen that when the combination of DX1002 and CBP was used to treat human lung cancer 95D, the tumor inhibitory rate was 86.85%, but when DX1002 and CBP were separately used, the tumor inhibitory rates were only 41.85% and 56.65%, respectively. Based on Q value calculated by Jin's formula, Q value of the combination of DX1002 and CBP (the weight ratio of them being 112:1) according to the present invention was 1.16, more than the synergistic limited value 1.15; in addition, the body weight of animals was not obviously reduced, and the obvious combined toxicity was also not found.

Results indicated that when treating small cell lung cancer, especially highly metastatic small cell lung cancer (95D), the combination of DX1002 and CBP according to the present invention can develop synergistic effects.

Example 2

The Therapeutic Effect of DX1002 Combined with PAC Against Human Lung Cancer A549 Transplanted in Nude Mice 1. Experimental Materials Reagents: Paclitaxel injection (PAC, batch number 15120024, specification 30 mg/5 ml), produced by Sichuan Taiji Pharmacutical Co. Ltd, diluted to the required concentration with sterile normal saline before use.

The preparative method of DX1002 was same to that in Example 1.

Animals: BALB/C nude mice (SPF grade, body weight: 19-21 g, male).

Animal number: 8 mice/group.

Tumor cell lines: human lung cancer A549 cell lines provided by West China Medical Center of Sichuan University.

2. Experimental Method

Well-grown lung cancer A549 tumor block was taken out, and cut into 3 mm equal blocks under sterile conditions. Each mouse was subcutaneously inoculated a block under right axilla with trocar. Four groups were included, and each test group has 8 mice, while the control group has more than 8 mice:

Group 1: DX1002 200 mg/kg/day (ig×21 d)

Group 2: PAC 5 mg/kg/day (ip×21 d, injected every other day)

Group 3: DX1002 200 mg/kg (ig×21 d)+ PAC 5 mg/kg (ip×21 d, qod)

Group 4: Control 14 days after inoculation, the mean volume of tumor block was found to be about 100 mm$^3$, and animals were regrouped based on the tumor size. Animals with too large or too small tumors were eliminated, and the mean tumor volume in each group was almost identical. Drugs were administrated as above schedule, and given by gavage for successive 21 days, with a volume of 0.5 ml/20 g body weight. Paclitaxel injection was intraperitoneally (ip) injected every other day for total 10 days, and the volume was 0.2 ml/20 g. From day 21 after inoculation, tumor long diameter a (mm), as well as its vertical short diameter b (mm), is measured twice a week using electronic digital caliper rule, and the calculation formula of tumor volume is $TV=ab^2/2$, while the calculation formula of relative tumor volume is $RTV=V_t/V_o$, in which $V_o$ is the tumor volume measured when caged (i.e. d1), and $V_t$ is the tumor volume measured every time. 29 days after inoculation, all animals were sacrificed. 3. Experimental Results Results are shown in Table 2. From Table 2, it can be seen that when the combination of DX1002 and paclitaxel was used to treat human lung cancer A549, the tumor inhibitory rate was 94.83%, but when DX1002 and paclitaxel were separately used, the tumor inhibitory rates were only 41.85% and 56.65%, respectively. Based on Q value calculated by Jin's formula, Q value of the combination of DX1002 and paclitaxel according to the present invention was 1.17, more than the synergistic limited value 1.15; in addition, the body weight of animals was not obviously reduced, and the obvious combined toxicity was also not found.

DX1002 and paclitaxel were separately used, the tumor inhibitory rates were only 61.08% and 51.96%, respectively. Based on Q value calculated by Jin's formula, Q value of the combination of DX1002 and paclitaxel (the weight ratio of them being 840:11) according to the present invention was 1.17, more than the synergistic limited value 1.15; in addition, the body weight of animals was not obviously reduced, and the obvious combined toxicity was also not found.

Results indicated that when treating lung cancer, the combination of DX1002 and paclitaxel according to the present invention can develop synergistic effects.

Example 3

The Therapeutic Effect of DX1002 Combined with Paclitaxel Against Human Tumor A2780 Transplanted in Nude Mice 1. Experimental Materials Reagents: Paclitaxel injection (PAC, batch number 15120024, specification 30 mg/5 ml), produced by Sichuan Taiji Pharmacutical Co. Ltd, diluted to the required concentration with sterile normal saline before use.

The preparative method of DX1002 was same to that in Example 1.

Animals: BALB/C nude mice (SPF grade, body weight: 19-21 g, male).

Animal number: 8 mice/group.

Tumor cell lines: human ovarian cancer A2780 cell lines provided by West China Medical Center of Sichuan University.

2. Experimental Method

Human ovarian cancer A2780 cell lines transplanted in nude mice were created by seeding human ovarian cancer A2780 cell lines under the skin of armpit. The inoculum amount of cells was 1×10$^6$, and after the transplanted tumor was formed, the tumor cells were further passed to the third generation before use. Tumor tissues at vigorous growth stage were taken out, and cut into about 1.5 mm$^3$ blocks. After homogenated under sterile conditions, cell suspension was prepared, and inoculated 0.1 ml in the right side of armpit under the skin in nude mice. For the mice-transplanted tumor, the diameter of transplanted tumor was measured using slide gauge, and after the tumor grew to 100 mm$^3$, animals were randomly divided into groups, six mice

TABLE 2

The tumor inhibitory effect of DX1002 combined with paclitaxel against human lung cancer A549 transplanted in nude mice ($\bar{x} \pm SD$)

| Group | Dose (mg/kg · ip) | Animal numbers beginning/end | Terminal weight (g) | RTV (d 21) | Tumor inhitory rate (%) | Q |
|---|---|---|---|---|---|---|
| Control | — | 6/6 | 23.8 ± 0.8 | 10.20 ± 1.75 | — | |
| paclitaxel | 5 × 11 | 6/6 | 23.8 ± 1.2 | 3.97 ± 0.90** | 61.08 | |
| DX1002 | 200 × 21 | 6/6 | 23.8 ± 3.0 | 4.90 ± 0.69** | 51.96 | |
| paclitaxel + DX1002 | 5 × 11 + 200 × 21 | 6/6 | 23.9 ± 1.9 | 0.527 ± 0.76** | 94.83 | 1.17 |

Compared with the control group:
*P < 0.05,
**P < 0.01.

From Table 2, it can be seen that when the combination of DX1002 and paclitaxel was used to treat human lung cancer A549, the tumor inhibitory rate was 94.83%, but when in each group. Using the procedures of measuring the tumor diameter, the antitumor effect of test substance was dynamically observed.

DX1002 was dissolved in water at a concentration of 10 mg/kg, and then successively poured into stomach through mouth every other day for three weeks; paclitaxel was intravenously injected at a dose of 10 mg/kg every other day for three weeks. The tumor diameter was measured every three days. The administration volume was 0.1 ml/20 g. The negative control received the same amount of normal saline by intravenous injection.

3. Experimental Results Experimental results are shown in Table 3:

TABLE 3

The tumor growth inhibitory effect of DX1002 combined with paclitaxel against human ovarian cancer A2780 transplanted in nude mice ($\bar{x} \pm SD$)

| Groups | Dose (mg/kg · ip) | Animal number beginning/end | Terminal body weight (g) | RTV (d 21) | Tumor inhibitory rate (%) | Q |
|---|---|---|---|---|---|---|
| Control | — | 6/6 | 23.5 ± 1.1 | 41.54 ± 17.32 | — | |
| Paclitaxel | 10 × 11 | 6/6 | 22.0 ± 0.6* | 18.48 ± 3.58* | 55.51 | |
| DX1002 | 10 × 11 | 6/6 | 21.8 ± 1.0* | 18.89 ± 6.10* | 54.53 | |
| Paclitaxel + DX1002 | 10 × 11 + 10 × 11 | 6/6 | 22.2 ± 1.1 | 3.24 ± 6.83** | 92.20 | 1.16 |

Compared with the control group:
*P < 0.05,
**P < 0.01.

From Table 3, it can be seen that when the combination of DX1002 and paclitaxel was used to treat human ovarian cancer A2780, the tumor inhibitory rate was 92.20%, but when DX1002 and paclitaxel were separately used, the tumor inhibitory rates were only 55.51% and 54.53%, respectively. Based on Q value calculated by Jin's formula, Q value of the combination of DX1002 and paclitaxel (the weight ratio of them being 1:1) according to the present invention was 1.16, more than the synergistic limited value 1.15; in addition, compared with their single use, the toxicity was obviously attenuated.

Results indicated that when treating ovarian cancer, the combination of DX1002 and paclitaxel according to the present invention can develop synergistic effects, and simultaneously reduce the toxicity too.

Example 4

The Therapeutic Effect of DX1002 Combined with Sorafenib Against Human Liver Cancer huh-7 Transplanted in Nude Mice 1. Experimental Materials Reagents: sorafenib (batch number BXGECL1, specification 200 mg/tablet), produced by Bayer healthcare Co. Ltd, Germany, diluted to the required concentration with sterile normal saline before use.

The preparative method of DX1002 was same to that in Example 1.

Animals: BALB/C nude mice (SPF grade, body weight: 19-21 g, male).

Animal number: 8 mice/group.

Tumor cell lines: human ovarian cancer A2780 cell lines provided by West China Medical Center of Sichuan University.

2. Experimental method

Human liver cancer huh-7 cell lines transplanted in nude mice were created by seeding human liver cancer huh-7 cell lines under the skin of armpit of nude mice. The inoculum amount of cells was $1 \times 10^6$, and after the transplanted tumor was formed, the tumor cells were further passed to the third generation before use. Tumor tissues at vigorous growth stage were taken out, and cut into about 1.5 mm³ blocks. After homogenated under sterile conditions, cell suspension was prepared, and inoculated 0.1 ml in the right side of armpit under the skin in nude mice. For the mice-transplanted tumor, the diameter of transplanted tumor was measured using slide gauge, and after the tumor grew to 100 mm³, animals were randomly divided into groups, six mice in each group. Using the procedures of measuring the tumor diameter, the antitumor effect of test substance was dynamically observed.

DX1002 was orally given at a dose of 100 mg/kg, once every other day, for three weeks; sorafenib was orally administrated at a dose of 20 mg/kg, once every other day, for three weeks. The tumor diameter was measured every three days. The negative control orally received the same amount of normal saline.

3. Experimental Results

Results are shown in Table 4:

TABLE 4

The tumor growth inhibitory effect of DX1002 combined with sorafenib against human liver cancer huh-7 transplanted in nude mice ($\bar{x} \pm SD$)

| Group | Dose (mg/kg · po) | Animal number beginning/end | Terminal body weight (g) | RTV (d 21) | Tumor inhibitory rate (%) | Q |
|---|---|---|---|---|---|---|
| Control | — | 6/6 | 23.2 ± 0.7 | 9.54 ± 2.88 | — | |
| Sorafenib | 20 × 11 | 6/6 | 22.4 ± 0.5 | 4.71 ± 1.53* | 50.63 | |
| DX1002 | 100 × 11 | 6/6 | 22.8 ± 1.0 | 3.93 ± 2.16* | 58.81 | |

TABLE 4-continued

The tumor growth inhibitory effect of DX1002 combined with sorafenib against
human liver cancer huh-7 transplanted in nude mice ($\bar{x} \pm SD$)

| Group | Dose (mg/kg · po) | Animal number beginning/end | Terminal body weight (g) | RTV (d 21) | Tumor inhibitory rate (%) | Q |
|---|---|---|---|---|---|---|
| Sorafenib + DX1002 | 10 × 11 + 100 × 11 | 6/6 | 23.2 ± 0.4 | 0.76 ± 1.51** | 92.03 | 1.16 |

Compared with the control group:
*P < 0.05,
**P < 0.01.

From Table 4, it can be seen that when the combination of DX1002 and sorafenib was used to treat human liver cancer huh-7, the tumor inhibitory rate was 92.03%, but when DX1002 and sorafenib were separately used, the tumor inhibitory rates were only 50.63% and 58.81%, respectively. Based on Q value calculated by Jin's formula, Q value of the combination of DX1002 and sorafenib (the weight ratio of them being 5:1) according to the present invention was 1.16, more than the synergistic limited value 1.15; in addition, compared with their single use, the toxicity was obviously attenuated.

Results indicated that when treating liver cancer, the combination of DX1002 and sorafenib according to the present invention can develop synergistic effects, and simultaneously reduce the toxicity too.

Example 5

The Therapeutic Effect of DX1002 Singly Used and Combined with CTX Against Mouse B16

1. Experimental Materials

Reagents: cyclophosphamide (CTX, batch number 15122125, specification 0.2 g), produced by Jiangsu Shengdi Pharmaceutical Co. Ltd, diluted to the required concentration with sterile normal saline before use.

The preparative method of DX1002 was same to that in Example 1.

Animals: BALB/C nude mice (SPF grade, body weight: 19-21 g, male).
Animal number: 8 mice/group.
Tumor cell lines: melanoma B16 cell lines provided by West China Medical Center of Sichuan University.

2. Experimental Method

For mouse melanoma B16 model, male C57BL/6 mice (18-22 g) were selected. During the experiment, well-grown tumor tissue was taken out, sheared, ground, filtered, and diluted with sterile normal saline at a volume ratio of 1:3, to prepare the suspension of tumor cells. Each mouse was inoculated 0.2 ml cell suspension in the back of armpit. On the next day after inoculation, animals were randomly divided into groups, weighed, and received drugs. The administration volume of cyclophosphamide injection was per 10 g mouse via intraperitoneal injection. For the single use or the combined use of cyclophosphamide, on the next day of inoculation, cyclophosphamide was injected once. DX1002 was orally given once every day for successive 13 days. For the combination group of DX1002 and cyclophosphamide, DX1002 was firstly injected to the left side of peritoneal cavity, and then cyclophosphamide was injected to the right side of peritoneal cavity.

Experimental animals were divided to four groups, i.e. the negative control group, the single-use group of 60 mg/kg cyclophosphamide, 5 mg/kg DX1002 group, and the combination group of 60 mg/kg cyclophosphamide and 5 mg/kg DX1002. Each group includes 10 mice. On the next day of DX1002 withdrawal, animals were sacrificed and weighed, then tumors were peeled and weighed. Based on the tumor weight, the tumor inhibitory rate (%) was calculated. Body weight and tumor weight were expressed as mean±SD (x), t test was carried out between each test group and the positive control group, the combination group and the single use group of cyclophosphamide.

3. Experimental Results
Results are shown in Table 5:

TABLE 5

The therapeutic effect of DX1002 singly used and
combined with CTX against mouse melanoma B16

| Group | Dose (mg/kg × times) | Animal number | Terminal body weight (g) | RTV | Tumor inhibitory rate (%) | Q |
|---|---|---|---|---|---|---|
| control | — | 10/10 | 22.69 ± 1.20 | 3.27 ± 0.59 | — | |
| CTX | 60 × 1 | 10/10 | 23.03 ± 1.34 | 1.38 ± 0.49* | 57.80 | |
| DX1002 | 5 × 13 | 10/10 | 22.47 ± 1.66 | 1.83 ± 0.72* | 44.04 | |
| DX1002/CTX | 5 × 13 + 60 × 1 | 10/10 | 22.35 ± 1.24 | 1.11 ± 0.53** | 89.30 | 1.17 |

Compared with the control group:
*P < 0.05,
**P < 0.01.

From Table 5, it can be seen that when the combination of DX1002 and cyclophosphamide was used to treat melanoma B16, the tumor inhibitory rate was 92.03%, but when DX1002 and cyclophosphamide were separately used, the tumor inhibitory rates were only 57.8% and 44.04%, respectively. Based on Q value calculated by Jin's formula, Q value of the combination of DX1002 and cyclophosphamide (the weight ratio of them being 65:60) according to the present invention was 1.16, more than the synergistic limited value 1.15; in addition, compared with their single use, the toxicity was obviously attenuated.

Results indicated that when treating melanoma, the combination of DX1002 and cyclophosphamide according to the present invention can develop synergistic effects, and simultaneously reduce the toxicity too.

Example 6

Effect of DX1002 Combined with Adriamycin on Mouse Liver Cancer 1122 Growth

1. Experimental Materials

Reagents: adriamycin (batch number 2160102, specification 10 mg), produced by Shanxi Pude Pharmaceutical Co. Ltd, diluted to the required concentration with sterile normal saline before use.

The preparative method of DX1002 was same to that in Example 1.

Animals: BALB/C nude mice (SPF grade, body weight: 19-21 g, male).

Animal number: 8 mice/group.

Tumor cell lines: liver cancer H22 cell lines provided by West China Medical Center of Sichuan University.

2. Experimental Methods

For mouse liver cancer H22 model, male Kunming mice (18-22 g) were selected. During the experiment, the murine ascetic fluid was drawn and diluted with sterile normal saline at a volume ratio of 1:3, to prepare the suspension of tumor cells. Each mouse was inoculated 0.2 ml cell suspension in the back of armpit. On the next day after inoculation, animals were randomly divided into groups, weighed, and received drugs.

Experimental animals were divided to four groups, i.e. the negative control group, the single-use injection group of 3 mg/kg adriamycin, 800 mg/kg DX1002 oral group, and the combination group of 3 mg/kg adriamycin and 800 mg/kg DX1002. On the next day of the last administration, animals were sacrificed and weighed, then tumors were peeled and weighed. Based on the tumor weight, the tumor inhibitory rate (%) was calculated. Body weight and tumor weight were expressed as mean±SD (x), and t test was carried out between each test group and the positive control group.

3. Experimental Results

Experimental results are shown in Table 6:

From Table 6, it can be seen that when the combination of DX1002 and adriamycin was used to treat liver cancer H22, the tumor inhibitory rate was 94.82%, but when DX1002 and adriamycin were separately used, the tumor inhibitory rates were only 57.67% and 57.02%, respectively. Based on Q value calculated by Jin's formula, Q value of the combination of DX1002 and adriamycin (the weight ratio of them being 4400:9) according to the present invention was 1.16, more than the synergistic limited value 1.15; in addition, the body weight of animals was not obviously reduced, and the obvious combined toxicity was also not found.

Experimental results indicated that when treating liver cancer, the combination of DX1002 and adriamycin according to the present invention can develop synergistic effects.

Example 7

The Therapeutic Effect of DX1002 Combined with TXT Against Mouse Lewis Lung Cancer Growth 1. Experimental Materials Reagents: docetaxel injection (TXT, batch number 16022115, specification 20 mg), produced by Jiangsu Hengrui Pharmaceutical Co. Ltd, diluted to the required concentration with sterile normal saline before use.

The preparative method of DX1002 was same to that in Example 1.

Animals: BALB/C nude mice (SPF grade, body weight: 19-21 g, male).

Animal number: 8 mice/group.

Tumor cell lines: Lewis lung cancer cell lines provided by West China Medical Center of Sichuan University.

2. Experimental Method

For mouse Lewis lung cancer model, male C57BL/6 mice (18-20 g) were selected. During the experiment, well-grown tumor tissue was taken out, sheared, ground, filtered, and diluted with sterile normal saline at a volume ratio of 1:3, to prepare the suspension of tumor cells. Each mouse was inoculated 0.2 ml cell suspension in the back of armpit. On the next day after inoculation, animals were randomly divided into groups, weighed, and received drugs. For the solvent control group, 0.2 ml normal saline was intraperitoneally injected to 10 g mouse, once every day. The administration volume of docetaxel injection (TXT) was that 10 g mouse received 0.2 ml via intraperitoneal injection, once every day. For the single use group or the combined use group of docetaxel, docetaxel was administrated for successive 5 days, and from day 6, the drug was removed. DX1002 was orally given once every day for successive 10 days.

TABLE 6

The growth inhibitory effect of DX1002 singly used and combined with adriamycin against mouse liver cancer H22

| Group | Dose (mg/kg × times) | Animal number beginning/end | Body weight (g) $\bar{x} \pm SD$ | Tumor weight (g) $\bar{x} \pm SD$ | Tumor inhibitory rate (%) | Q |
|---|---|---|---|---|---|---|
| control | | 10/10 | 27.6 ± 3.6 | 4.63 ± 0.73 | — | |
| adriamycin | 3 × 6 | 10/10 | 21.4 ± 3.5* | 1.96 ± 0.47* | 57.67* | |
| DX1002 | 800 × 11 | 10/10 | 27.2 ± 2.9 | 1.99 ± 0.53* | 57.02 | |
| DX1002 + AMD | 800 × 11 + 3 × 6 | 10/10 | 20.4 ± 2.2** | 0.24 ± 0.41** | 94.82** | 1.16 |

Compared with the control group:
*P < 0.05,
**P < 0.01.

Experimental animals were divided to four groups, i.e. the negative control group, the single-use group of 15 mg/kg docetaxel, 1600 mg/kg DX1002 group, and the combination group of 15 mg/kg docetaxel and 1600 mg/kg DX1002. Each group includes 10 mice. On the next day of DX1002 withdrawal, animals were sacrificed and weighed, then tumors were peeled and weighed. Based on the tumor weight, the tumor inhibitory rate (%) was calculated. Body weight and tumor weight were expressed as mean±SD ($\bar{x}$), and t test was carried out between each test group and the positive control group, the combination group and the single use group of docetaxel.

3. Experimental Results

Experimental results are shown in Table 7. From Table 7, it can be seen that when the combination of DX1002 and docetaxel was used to treat Lewis lung cancer, the tumor inhibitory rate was 89.61%, but when DX1002 and docetaxel were separately used, the tumor inhibitory rates were only 50.28% and 53.65%, respectively. Based on Q value calculated by Jin's formula, Q value of the combination of DX1002 and docetaxel (the weight ratio of them being 640:1) according to the present invention was 1.16, more than the synergistic limited value 1.15; in addition, the body weight of animals was not obviously reduced, and the obvious combined toxicity was also not found.

TABLE 7

The growth inhibitory effect of DX1002 singly used and combined with docetaxel against mouse Lewis lung cancer.

| Group | Dose (mg/kg) | Animal number beginning/end | Body weight (g) ($\bar{x}$ ± SD) | Tumor weight (g) ($\bar{x}$ ± SD) | Tumor inhibitory rate (%) | Q |
|---|---|---|---|---|---|---|
| control | — | 10/10 | 18.41 ± 2.39 | 3.56 ± 0.45 | — | |
| TXT | 5 × 5 | 10/10 | 15.5700.72** | 1.77 ± 0.52** | 50.28 | |
| DX1002 | 1600 × 10 | 10/10 | 20.4611.23** | 1.65 ± 0.62** | 53.65 | |
| DX1002 + TXT | 1600 × 10 + 5 × 5 | 10/10 | 15.5510.92** | 0.37 ± 0.31** | 89.61 | 1.16 |

Compared with the control group:
*P < 0.05,
**P < 0.01.

From Table 7, it can be seen that when the combination of DX1002 and docetaxel was used to treat Lewis lung cancer, the tumor inhibitory rate was 89.61%, but when DX1002 and docetaxel were separately used, the tumor inhibitory rates were only 50.28% and 53.65%, respectively. Based on Q value calculated by Jin's formula, Q value of the combination of DX1002 and docetaxel (the weight ratio of them being 640:1) according to the present invention was 1.16, more than the synergistic limited value 1.15; in addition, the body weight of animals was not obviously reduced, and the obvious combined toxicity was also not found.

Experimental results indicated that when treating lung cancer, the combination of DX1002 and docetaxel according to the present invention can develop synergistic effects.

Example 8

The Therapeutic Effect of DX1002 Combined with BON Against Human Colon Cancer HT-29

1. Experimental Materials

Reagents: bleomycin hydrochloride (BON, batch number 151102, specification 1.5 million units), produced by Co. Ltd, diluted to the required concentration with sterile normal saline before use.

The preparative method of DX1002 was same to that in Example 1.

Animals: BALB/C nude mice (SPF grade, body weight: 19-21 g, male).

Animal number: 8 mice/group.

Tumor cell lines: Human colon cancer HT-29 cell lines provided by West China Medical Center of Sichuan University.

2. Experimental Method

Well-grown colon cancer HT-29 tumor block was taken out, and cut into 3 mm equal blocks under sterile conditions. Each mouse was subcutaneously inoculated a block under right axilla with trocar. Four groups were included, and each test group has 8 mice, while the control group has more than 8 mice:

Group 1: DX1002 200 mg/kg/day (ig, qd×14)
Group 2: BON 1 mg/kg (ip, qod×14)
Group 3: DX1002 200 mg/kg (ig, qd×14)+ CBP 1 mg/kg (ip, qod×14)
Group 4: Control 14 days after inoculation, the mean volume of tumor block was found to be about 100 mm$^3$, and animals were regrouped based on the tumor size. Animals with too large or too small tumors were eliminated, and the mean tumor volume in each group was almost identical. Drugs were administrated as above schedule, and poured into stomach through mouth for successive 14 days, with a volume of 0.5 ml/20 g body weight. BON was intraperitoneally injected every other day for successive 14 days, and the volume was 0.2 ml/20 g. From day 14 after inoculation, tumor long diameter, as well as its vertical short diameter, is measured twice a week using electronic digital caliper rule. 29 days after inoculation, all animals were sacrificed.

3. Experimental Results

Experimental results are shown in Table 8:

TABLE 8

The tumor inhibitory effect of DX1002 combined with BON against human colon cancer HT-29 transplanted in nude mice ($\bar{x} \pm SD$)

| Group | Dose (mg/kg) | Animal number beginning/end | Body weight of animals | RTV (d 15) | Tumor inhibitory | Q |
|---|---|---|---|---|---|---|
| Control | — | 16/15 | 24.0515 | 20.7115 | — | — |
| BON | 1 × 7 | 8/8 | 24.2685 | 8.16685 | 48.87 | — |
| DX1002 | 200 × 14 | 8/8 | 23.0085 | 11.2985 | 50.31 | — |
| DX1002 + BON | 200 × 14 + 1 × 7 | 8/8 | 24.238 Ipx | 7.8438 Ip × 1 | 86.29 | 1.16 |

Compared with the control group:
*P < 0.05,
**P < 0.01.

From Table 8, it can be seen that when the combination of DX1002 and bleomycin hydrochloride was used to treat colon cancer HT-29, the tumor inhibitory rate was 86.29%, but when DX1002 and bleomycin hydrochloride were separately used, the tumor inhibitory rates were only 48.87% and 5.31%, respectively. Based on Q value calculated by Jin's formula, Q value of the combination of DX1002 and bleomycin hydrochloride (the weight ratio of them being 400:1) according to the present invention was 1.16, more than the synergistic limited value 1.15; in addition, the body weight of animals was not obviously reduced, and the obvious combined toxicity was also not found.

Experimental results indicated that when treating colon cancer, the combination of DX1002 and bleomycin hydrochloride according to the present invention can develop synergistic effects.

The joint use of trans-styrene acid derivatives and antitumor drugs according to the present invention can provide synergistic action, and the use of trans-styrene acid derivatives combined with a part of antitumor drugs can further exert the toxicity attenuation effects. The therapeutic effect of drug combination prepared with trans-styrene acid derivatives and antitumor drugs is good, and the toxicity is low, with a good clinical application prospect.

The invention claimed is:

1. A drug combination comprising a styrene acid derivative, an antitumor medicament, and a pharmaceutically acceptable carrier,
   wherein said styrene acid derivative is (E)-3-(2',3'-dihydroxyl-4'-methoxylphenyl)-2-(3",4",5"-trimethoxylphenyl)-2-acrylic acid and said antitumor medicament is selected from the group consisting of carboplatin, paclitaxel, sorafenib, cyclophosphamide, adriamycin, docetaxel, and bleomycin hydrochloride.

2. The drug combination according to claim 1, wherein a weight ratio of the styrene acid derivative and the antitumor medicament is in a range of 1:1 to 640:1.

3. The drug combination according to claim 2, wherein:
   when the antitumor drug is carboplatin, the weight ratio of the styrene acid derivative and the antitumor medicament is 112:1;
   when the antitumor drug is paclitaxel, the weight ratio of the styrene acid derivative and the antitumor medicament is in the range of 1:1-840:11;
   when the antitumor drug is sorafenib, the weight ratio of the styrene acid derivative and the antitumor medicament is 5:1;
   when the antitumor drug is cyclophosphamide, the weight ratio of the styrene acid derivative and the antitumor medicament is 65:60;
   when the antitumor drug is adriamycin, the weight ratio of the styrene acid derivative and the antitumor medicament is 4400:9;
   when the antitumor drug is docetaxel, the weight ratio of the styrene acid derivative and the antitumor medicament is 640:1; and
   when the antitumor drug is bleomycin hydrochloride, the weight ratio of the styrene acid derivative and the antitumor medicament is 400:1.

4. The drug combination according to claim 1, effective in treating lung cancer, liver cancer, ovarial caner, melanoma, colon cancer, kidney cancer, or bladder cancer.

5. The drug combination according to claim 1, effective in treating small cell lung cancer.

6. A method for preparing the drug combination of claim 1, comprising mixing a styrene acid derivative, an antitumor medicament, and a pharmaceutically acceptable carrier,
   wherein the styrene acid derivative is (E)-3-(2',3'-dihydroxyl-4'-methoxylphenyl)-2-(3",4",5"-trimethoxylphenyl)-2-acrylic acid and antitumor medicament is selected from the group consisting of carboplatin, paclitaxel, sorafenib, cyclophosphamide, adriamycin, docetaxel, and bleomycin hydrochloride.

* * * * *